United States Patent
Lang et al.

(10) Patent No.: US 6,830,747 B2
(45) Date of Patent: Dec. 14, 2004

(54) BIODEGRADABLE COPOLYMERS LINKED TO SEGMENT WITH A PLURALITY OF FUNCTIONAL GROUPS

(75) Inventors: Meidong Lang, Ann Arbor, MI (US); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 237 days.

(21) Appl. No.: 10/101,408

(22) Filed: Mar. 20, 2002

(65) Prior Publication Data

US 2003/0027940 A1 Feb. 6, 2003

Related U.S. Application Data

(60) Provisional application No. 60/288,806, filed on May 7, 2001.

(51) Int. Cl.[7] .......................... A61F 2/06; A61K 47/40; A61K 31/74; C08G 63/91; C08G 65/329
(52) U.S. Cl. ................. 424/78.17; 424/78.18; 424/78.19; 424/78.21; 525/185; 525/186; 525/188; 525/190; 525/411; 525/412; 525/415; 525/418; 525/450; 623/1.42
(58) Field of Search .................. 525/185, 106, 525/180, 190, 411, 412, 415, 418, 450; 424/78.17, 78.18, 78.19, 78.21; 623/1.42

(56) References Cited

U.S. PATENT DOCUMENTS

| 4,132,735 A | * | 1/1979 | Lamberti et al. ............ 562/582 |
| 5,516,881 A | | 5/1996 | Lee et al. ................... 528/320 |
| 5,629,384 A | * | 5/1997 | Veronese et al. ........ 525/326.8 |

FOREIGN PATENT DOCUMENTS

| FR | 9308783 | * | 1/1995 |
| WO | WO02/18477 | | 3/2002 |

OTHER PUBLICATIONS

Lang, M., et al, J. Biomater. Sci. Polymer Edn., vol. 10, No. 4, 501–512 (1999).

Lang, M., et al., Journal of Polymer Science: Part A: Polymer Chemistry, vol. 39, 4214–4226 (2001).

* cited by examiner

*Primary Examiner*—Ana Woodward

(57) ABSTRACT

Biocompatible biodegradable polymer or copolymer is capped at one end and has free hydroxyl at the other end. The free hydroxyl can be reacted to link a plurality of functional groups some or each of which can be reacted to attach directly or via a spacer molecule a moiety containing an aminoxyl-containing radical or to a moiety comprising other drug molecule residue or a moiety comprising other biologically active agent residue.

23 Claims, No Drawings

US 6,830,747 B2

BIODEGRADABLE COPOLYMERS LINKED TO SEGMENT WITH A PLURALITY OF FUNCTIONAL GROUPS

CROSS-REFERENCE TO RELATED APPLICATION

This application claims the benefit of U.S. Provisional Application No. 60/288,806, filed May 7, 2001, the whole of which is incorporated herein by reference.

TECHNICAL FIELD

This invention is directed to providing biocompatible biodegradable polymers or copolymers linked to a plurality of functional groups and the products resulting from reaction of some or each of the functional groups to attach moieties containing aminoxyl-containing radicals or comprising other drug molecule residues or other biologically active agent residues.

BACKGROUND OF THE INVENTION

Aliphatic polyesters are a group of biomaterials that have commercially successful application because of their biodegradability and biocompatibility. Although these polymers have been used extensively as sutures, implant materials and drug carriers, they do not have any inherent biological functions to actively participate in human body repair.

Nitric oxide has become one of the most studied compounds in biochemistry and biology, and this compound and its biological functions are the subject of many reviews. However, excessive introduction of nitric oxide into the body may have adverse side effects such as microvascular leakage, tissue damage, septic shock, B-cell destruction and possible mutagenic risk. Therefore, it is important to control nitric oxide concentration and release.

Lee et al. U.S. Pat. No. 5,516,881 is directed to providing a nitric oxide-like stable free radical in the form of an aminoxyl-containing radical at the chain end of a polymer or copolymer including aliphatic polyester, as an approach to controlling nitric oxide concentration and release. The resulting product is limited in terms of the concentration of aminoxyl-containing radical available.

SUMMARY OF THE INVENTION

It has been discovered herein that biocompatible biodegradable polymers or copolymers allowing flexibility in available concentration of attached aminoxyl group or attached drug residue or attached biologically active agent residue is provided by providing a plurality of moieties containing aminoxyl-containing moiety or other drug molecule residue or other biologically active agent residue covalently or ionicly attached thereto.

One embodiment of the invention, denoted the first embodiment, is directed to a biocompatible biodegradable copolymer comprising a polymeric or copolymeric segment containing hydrolyzable ester or nitrogen-phosphorus linkage and which is capped at one end and linked at the other end to a polymeric or copolymeric segment having a plurality of functional groups pendant thereto, some or each of the functional groups being reacted to attach a moiety containing an aminoxyl-containing radical or to attach a moiety comprising other drug molecule residue or other biologically active agent residue.

Another embodiment of the invention, denoted the second embodiment, is directed to a biocompatible biodegradable polymer or copolymer which is capped at one end and has a free hydroxyl at the other end. The free hydroxyl can be reacted to attach moiety with unsaturation therein which in turn can be reacted to provide end segment with a plurality of functional groups thereon. Some or each of the functional groups can be reacted to attach a moiety containing an aminoxyl-containing radical or to attach a moiety comprising other drug molecule residue or other biologically active agent residue.

In still another embodiment herein, denoted the third embodiment, there is provided an admixture of biocompatible biodegradable polymer or copolymer which is capped at one end and contains at the other end a segment or segments with a plurality of functional groups thereon and a spin label and/or other drug molecule and/or other biologically active agent, e.g. in a weight ratio ranging from 1:99 to 99:1 polymer or copolymer to spin label, other drug molecule and other biologically active agent, to form a polymer drug matrix, for delivering the spin label, other drug and/or other biologically active agent, e.g. with controlled, e.g. sustained or delayed, release functionality.

In still another embodiment of the invention herein, denoted the fourth embodiment, there is provided a drug release system for biomedical application comprising the copolymer of the first embodiment or the admixture, polymer drug matrix, of the third embodiment.

In yet another embodiment of the invention herein, denoted the fifth embodiment, a stent is coated with the drug release system of the fourth embodiment to provide a drug eluting coating on the stent.

The term "biocompatible" is used herein to mean material that interacts with the body without undesirable aftereffects.

The term "biodegradable" is used to mean capable of being broken down into innocuous products in the normal functioning of the human body, tissues and cells and living organisms (e.g., bacteria).

The term "aminoxyl" is used herein to refer to the structure >N—O.. The term "aminoxyl-containing radical" is used herein to refer to a radical that contains the structure >N—O..

The term "moiety comprising other drug molecule residue" is used herein to refer to moiety comprising drug molecule minus any portion thereof separated on attachment to become part of the biocompatible biodegradable copolymer. The word "other" means that the drug does not contain a group containing the aminoxyl structure. The term "drug" is used herein to mean a substance for use in the diagnosis, cure, mitigation, treatment or prevention of disease.

The term "other biologically active agent" includes proteins, cytokines, oligonucleotides including antisense oligonucleotides, genes, carbohydrates and hormones, but excludes compounds containing an aminoxyl containing radical and "other drug molecules." The term "residue" is used to mean said agent minus any portion of the biologically active agent separated on attachment to become part of the biocompatible biodegradable polymer or copolymer.

DETAILED DESCRIPTION

We turn now to the first embodiment of the invention, which is directed to a biocompatible biodegradable copolymer comprising a polymeric or copolymeric segment containing hydrolyzable ester or nitrogen-phosphorus linkage and which is capped at one end and linked at the other end to a polymeric or copolymeric segment having a plurality of functional groups pendant thereto, some or each of the functional groups being reacted to attach a moiety containing an aminoxyl-containing radical or to attach a moiety comprising other drug molecule residue or other biologically active agent residue.

The weight average molecular weight of the biocompatible biodegradable copolymer of the first embodiment can range, for example, from about 750 to about 500,000.

An intermediate for providing the first embodiment is a biocompatible biodegradable polymer or copolymer which is capped at one end and has a free hydroxyl at the other end. The free hydroxyl is to react to incorporate an unsaturated group to provide a double bond functionalized (e.g., terminated) polymer or copolymer which in turn is to react to provide linkage to polymer containing the plurality of functional groups and which is formed by polymerizing unsaturated functional group containing compound in the presence of the double bond functionalized polymer or copolymer. The capping at the one end is to prevent the intermediate from cross-linking into insoluble form during its reaction with unsaturated functional group containing compound which would make a further step to react some or each of the functional groups with spin label to produce moiety containing aminoxyl-containing radical or with drug or drug derivative to produce moiety comprising other drug molecule residue or with other biologically active agent or derivative thereof to produce moiety comprising other biologically active agent residue, which is carried out in solution, difficult.

Said intermediate can be prepared by forming polymer or copolymer which would have hydroxyl groups at both ends in the presence of capping agent in sufficient amount to cap at one end but not at the other.

Polymers or copolymers which can be formed in the presence of capping agent to provide the intermediate include linear aliphatic polyesters, such as polylactones and copolymers thereof for example, polylactide, polycaprolactone, polyglycolic acid or poly(3-hydroxybutyrate) and their copolymers.

Poly(lactide-co-ε-caprolactone) is preferred over polylactide homopolymers because it provides better drug penetratability, i.e., better release of aminoxyl radical or drug or other biologically active agent from and through the polymer/copolymer and better elasticity. Poly(lactide-co-ε-caprolactone) is preferred over polycaprolactone homopolymers because the biodegradation rate of the copolymer is faster than that of the homopolymer and can be controlled by the ratio of lactide to caprolactone.

Still other polymers or copolymers which are to be capped at one end to provide said intermediate include those listed in Lee et al. U.S. Pat. No. 5,516,881, the entire disclosure of which is incorporated herein by reference. These include poly[bis(carboxylatophenoxy)phosphazine] which includes hydrolyzable nitrogen-phosphorus linkage. When the starting material polymers or copolymers listed in U.S. Pat. No. 5,516,881 contain carboxyl end groups, these can be converted to hydroxy end groups, e.g., by reaction with diol or anhydride.

Still other polymers for the intermediate include polyester-amide denoted PEA and poly(ester urethane) denoted PEUR as described in U.S. application Ser. No. 09/651,338 including a combination of poly(lactide-co-ε-caprolactone) with PEA/PEUR.

The capping agent is preferably a high boiling point (e.g., boiling point over 160° C.) single-hydroxy alcohol. The preferred single-hydroxy alcohol capping agent is benzyl alcohol, and it is preferred because it is not easily evaporated under conditions (e.g., high vacuum condition) where starting polymer is preferably synthesized and because its incorporation as benzyl ester end group is easily detected, e.g., by NMR. Other examples of single-hydroxy alcohol capping agents include cyclohexanol, cyclopentanol, cyclopentanemethanol, cycloheptanol and 3-cyclopentyl-1-propanol.

The weight average molecular weight of said intermediate can range, for example, from 500 to 30,000, e.g., from 1,000 to 20,000, for example, from 2,600 to 6,000.

The free hydroxyl on said intermediate for providing the first embodiment, is advantageously reacted, as indicated above, to incorporate an unsaturated group to provide a double bond functionalized polymer or copolymer which in turn is to react to provide linkage to polymer containing the plurality of functional groups, i.e., where the provision of the linkage at the other end (the non-capped end) comprises incorporating an unsaturated group to provide a double bond functionalized polymer or copolymer and providing linked segment having a plurality of functional groups pendant thereto by polymerizing unsaturated group containing functional group containing monomer in the presence of the double bond functionalized polymer or copolymer or by reacting unsaturated group containing compound with a plurality of said functional groups with the unsaturated group of the double bond functionalized polymer or copolymer. Some or each of the functional groups is to react to provide attachment to moiety containing an aminoxyl-containing radical or to moiety comprising other drug molecule residue or other biologically active agent residue.

The functional groups for the first embodiment can be, for example, carboxyl groups, amino groups or hydroxyl groups.

We turn now to the case where the functional groups are carboxyl groups. In this case, some or each of the carboxyl groups is reacted to attach via an amide, ester or oxycarbonyl linkage or carboxylate ion via ionic bonds a moiety containing an aminoxyl-containing radical or a moiety comprising other drug molecule residue or a moiety comprising other biologically active agent residue, and the weight average molecular weight of the biocompatible biodegradable copolymer ranges, for example, from 1,000 or 2,000 to 200,000, for example, from 2,500 to 16,500.

For the case where the plurality of functional groups are carboxyl groups, the biocompatible biodegradable polymer can be formed from a starting material polymer or copolymer which contains a hydrolyzable ester or nitrogen-phosphorus linkage and which is capped at one end and has a free hydroxyl at the other end by converting the hydrogen of the free hydroxyl to carbonyl linked to terminal moiety containing unsaturated group and reacting unsaturated group of the terminal moiety, i.e., the double bond functionalized polymer or copolymer, with unsaturated group containing compound or polymer thereof to provide an end segment with a plurality of carboxyl groups thereon and modifying some or each of the carboxyl groups to provide a moiety containing an aminoxyl-containing radical or a moiety comprising other drug molecule residue or other biologically active agent residue in place of the hydroxyl moiety of carboxyl group.

The provision of the double bond functionalized polymer or copolymer consistent with pendant carboxyl functional groups is, by reaction of the starting material polymer or copolymer, for example, with maleic anhydride or with methacryloyl or acryloyl compounds, e.g., methacryloyl chloride or acryloyl chloride, or with allyl isocyanate.

The reaction of unsaturated group of the terminal moiety of the double bond functionalized polymer or copolymer to provide an end segment with a plurality of carboxyl groups thereon, can be carried out by free radical polymerizing double bond containing carboxylic acid, e.g., acrylic acid or methacrylic acid, in the presence of the double bond terminated polymer or copolymer.

Each carboxyl functional group can be reacted to provide a moiety containing an aminoxyl-containing radical by reacting spin label suitable to replace hydroxy in the carboxyl with imino linked to the four position of 2,2,6,6-tetramethylpiperidine-1-oxy or with imino linked to the three position of 2,2,5,5-tetramethylpiperidine-1-oxy or with oxy linked to the carbonyl of 2,2,5,5-tetramethyl-3-pyrroline-1-oxy-3-carbonyl. Suitable spin labels are listed in U.S. Pat. No. 5,516,881.

Some or each of the carboxyl functional groups can be reacted to provide a moiety comprising other drug molecule residue or other biologically active agent residue in place of the hydroxyl moiety of carboxyl group by reacting drug or other biologically active agent with group(s) thereon reactable with said carboxyl group, e.g., an amine group or oxy linked to carbonyl or carboxylate or carboxylic acid or which are modified to contain such group(s).

We turn now to a case where the carboxyl functional group containing copolymer is poly(lactide-co-ε-caprolactone) which is capped at one end and is linked at the other end to a segment comprising polyacrylic acid and/or other polyacid which has carboxyl functional groups which can be reacted to attach a moiety containing aminoxyl-containing radical or a moiety comprising the drug molecule residue or other biologically active agent residue in place of hydroxyl group of carboxyl functional group.

In a preferred case, the polymeric or copolymeric segment is poly(lactide-co-ε-caprolactone) which is capped at one end, e.g., using benzyl alcohol, and is linked at the other end to a segment comprising polyacrylic acid with some or each of the carboxyl groups thereon modified to provide a moiety containing an aminoxyl-containing radical or a moiety comprising other drug molecule residue or other biologically active agent residue in place of the hydroxyl moiety of carboxyl group. For this case, the weight average molecular weight of the biocompatible biodegradable copolymer ranges, for example, from 1,000 to 150,000, for example from 3,200 to 13,000.

The weight average molecular weight for the poly(lactide-co-ε-caprolactone) intermediate which is capped at one end and is hydroxyl terminated at the other end can range, for example, from 1,000 to 20,000, for example, from 2,600 to 6,000.

In a very preferred case, the linking is provided by reacting maleic anhydride with hydroxyl of poly(lactide-co-ε-caprolactone) which is capped at one end and is hydroxyl terminated at the other end to provide a double bond functionalized poly(lactide-co-ε-caprolactone) and free radical polymerizing acrylic acid in the presence of the double bond terminated poly(lactide-co-ε-caprolactone). The resulting copolymer is a block copolymer where A blocks are random copolymer of lactide and ε-caprolactone and B block is polyacrylic acid. The resulting copolymer may be considered a graft copolymer with poly(acrylic acid) as a main backbone and capped poly(lactide-co-ε-caprolactone) as graft segments.

A very preferred biocompatible biodegradable copolymer can be prepared in a four step process as described below.

In a first step, there is prepared the intermediate poly(lactide-co-ε-caprolactone) which is capped with benzyl alcohol at one end and has one free hydroxyl at the other end, denoted herein as PBLC-OH where "P" stands for copolymer, "B" stands for the benzyl alcohol capping agent, "L" stands for lactide starting material, "C" stands for ε-caprolactone starting material, and —OH stands for the free hydroxyl. This first step is described in Lang, M., et al. J. Biomat. Sci. Polymer Edn. 10, No. 4, 501–512 (1999). The reaction of this step is the melt ring opening copolymerization of lactide and ε-caprolactone (2.5:1 molar ratio) in the presence of benzyl alcohol (trace) and stannous octoate which catalyzes the ring opening, carried out at 130° C. for 48 hours in a silanized polymerization tube. Ring opening catalysts which can be used in place of stannous octoate include, for example, aluminum triisopropoxide, $[(n-C_4H_9O)_2AlO]_2$ Zn, dibutyltin dimethoxide, Zn L-lactate, aluminum thiolates and triethylaluminum.

In a second step where unsaturated group is incorporated into the hydroxyl end of the product of the first step, the PBLC-OH is used as the precursor for the synthesis of double bond functionalized poly(lactide-co-ε-caprolactone) by reaction of the hydroxyl functionality of the PBLC-OH with maleic anhydride to provide the double bond functionalized poly(lactide-co-ε-caprolactone), which may be referred to maleic acid end capped poly(lactide/ε-caprolactone) copolymer, denoted herein as PBLC-Ma where "PBLC" is translated as above and "Ma" stands for the maleic acid end cap. The molar ratio of PBLC-OH to maleic anhydride is 5:1 and the reaction is carried out under $N_2$ in melt at 130° C. for 24 hours.

In a third step which constitutes the copolymerization of polymer product of the second step with acrylic acid, the PBLC-Ma and acrylic acid are subjected to free radical polymerization conditions to link polyacrylic acid segment and form acrylic acid/lactide/ε-caprolactone, which is denoted herein as PBLCA where the "A" stands for the polyacrylic acid segment. The reaction is initiated using 2,2'-azobisisobutyronitrile (AIBN) or other initiator agent and is carried out in dioxane with heating to 60° C. for 5 hours. The reaction product may be considered a graft copolymer with polyacrylic acid as a main backbone and PBLC as graft segments.

In a fourth step, aminoxyl radical containing moiety is incorporated into carboxylic acid sites of the PBLCA by reaction of 4-amino-2,2,6,6-tetramethylpiperidine-1-oxy (TEMPAMINE) with PBLCA so that imino from 4-amino replaces hydroxyl of carboxylic acid. This reaction is carried out in dioxane at 50° C. or in other suitable aprotic or other solvent for PBLCA, e.g., tetrahydrofuran, dimethyl sulfoxide or chloroform, in the presence of N,N'-carbonyl diimidazole to produce aminoxyl radical incorporated biocompatible biodegradable copolymer, denoted TAM-PBLCA where "TAM" stands for the TEMPAMINE reactant and "PBLCA" stands for the PBLCA reactant.

The product of the third step can also be used as a drug delivery matrix by admixing it with spin label, or other drug molecule or other biologically active agent.

The four-step reaction scheme for preparing the very preferred biocompatible biodegradable polymer is set forth below:

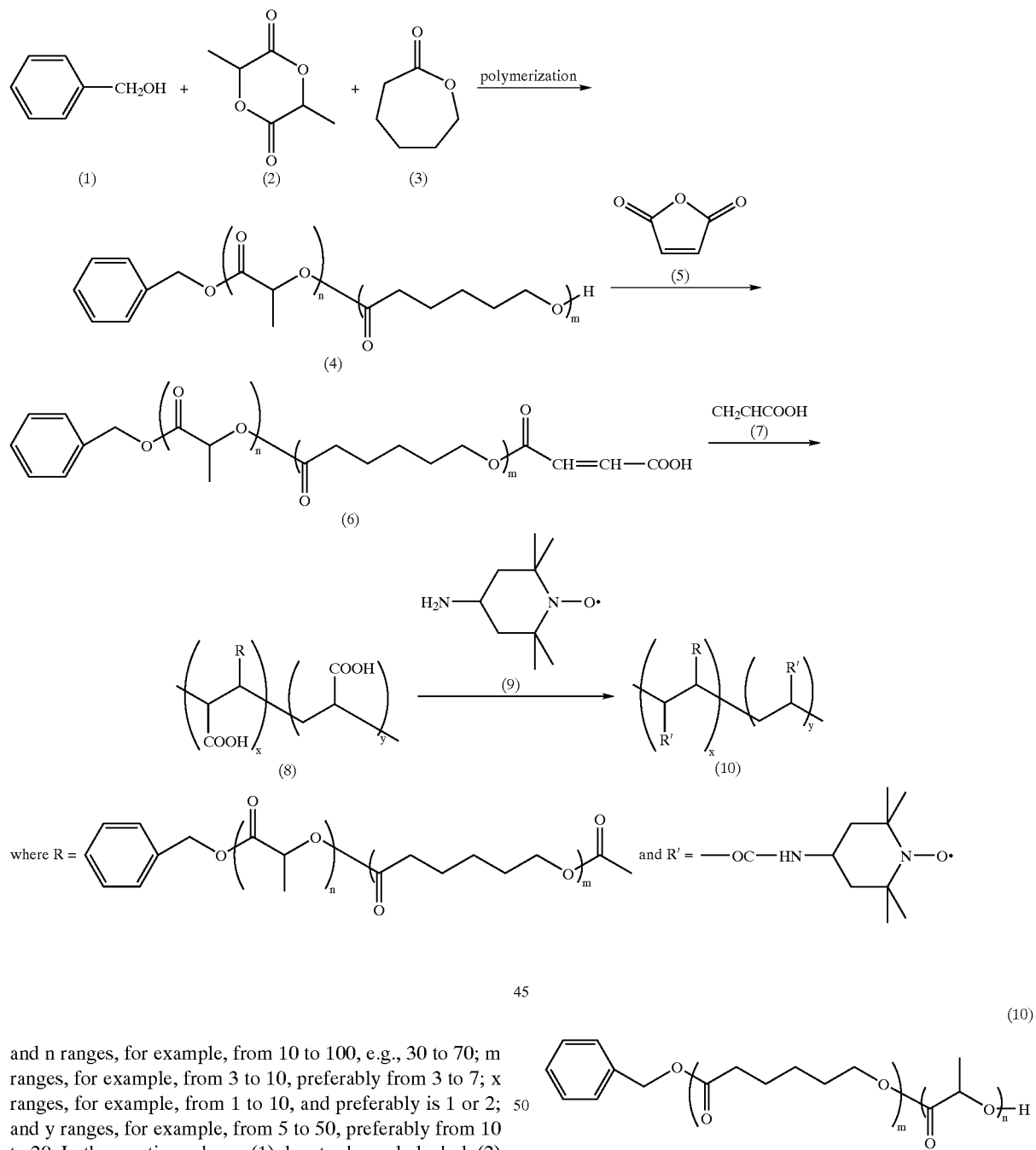

and n ranges, for example, from 10 to 100, e.g., 30 to 70; m ranges, for example, from 3 to 10, preferably from 3 to 7; x ranges, for example, from 1 to 10, and preferably is 1 or 2; and y ranges, for example, from 5 to 50, preferably from 10 to 20. In the reaction scheme (1) denotes benzyl alcohol, (2) denotes lactide, (3) denotes ε-caprolactone, (4) denotes PBLC-OH which is benzyl alcohol end capped random copolymer of lactide and ε-caprolactone, (5) denotes maleic anhydride, (6) denotes PBLC-Ma, (7) denotes acrylic acid, (8) denotes PBLCA, (9) denotes TEMPAMINE, and (10) denotes TAM-PBLCA.

Whereas (4) suggests an ε-caprolactone ending group, the PBLC-OH intermediate can also have a lactide unit as the ending group and in the working example hereinafter, 95% of the PBLC-OH copolymer had α-oxypropionyl end group (i.e., lactide unit). A structure showing PBLC-OH with lactide unit as the ending group is Moreover, in the reaction with maleic anhydride in the working example, some of the maleic acid monoester acid was rearranged (i.e., 13% of the double bond in PBLC-Ma) from maleic acid monoester to fumaric acid monoester.

We turn now to the cases where the functional groups pendant to the copolymeric segment are amine groups or hydroxyl groups. The reactant used in place of maleic anhydride can be reactant suitable to provide unsaturation and consistent with the functional group of unsaturated group containing monomer used in place of acrylic acid for providing a plurality of the functional groups on polymerization. In this case, the weight average molecular weight of the biocompatible biodegradable copolymer ranges, for example, from 1,000 or 2,000 to 200,000, for example from 2,500 to 16,500.

Utilities for the first embodiment herein, where the copolymer contains aminoxy-containing radical, include the antitumor treatment and blood vessel reconstruction as described in U.S. Pat. No. 5,516,881. Utilities for the first embodiment herein also include drug controlled release functionality including the utilities of the fourth and fifth embodiments herein.

We turn now to the second embodiment of the invention, which is directed to a biodegradable polymer or copolymer which is capped at one end and has a free hydroxyl at the other end. The polymer or copolymer of this embodiment is useful as an intermediate for providing the first embodiment. The polymer or copolymer and its preparation are described above in respect to the description of the first embodiment and its preparation and is referred to above as an intermediate for providing the first embodiment. The weight average molecular weight for the polymer or copolymer of the second embodiment can range, for example, from 500 to 30,000, e.g., from 1,000 to 20,000, for example from 2,600 to 6,000.

We turn now to the third embodiment of the invention herein, which is directed to an admixture of biocompatible biodegradable polymer or copolymer which is capped at one end and contains at the other end a segment or segments with a plurality of functional groups thereon and a spin label and/or other drug molecule or other biologically active agent forming a polymer drug matrix for delivering the spin label, other drug, or other biologically active agent, e.g., with controlled, e.g., sustained or delayed, release. The linking to the segment or segments with a plurality of functional groups thereon is preferably provided by incorporating in the polymer or copolymer and providing linked segment with a plurality of functional groups by polymerizing unsaturated group monomer in the presence of the double bond functionalized polymer or copolymer as described in conjunction with the first embodiment herein. Preferably, the biocompatible biodegradable polymer or copolymer for the third embodiment is formed from a starting material polymer or copolymer which contains a hydrolyzable ester or nitrogen-phosphorus linkage and which is capped at one end and has a free hydroxyl at the other end and converting the hydrogen of the free hydroxyl to carbonyl linked to terminal moiety containing unsaturated group and reacting unsaturated group of the terminal moiety with unsaturated carboxyl group containing compound or polymer thereof to provide an end segment with a plurality of carboxyl groups thereon, as described in conjunction with the first embodiment. A very preferred polymer or copolymer which is capped at one end and contains at the other end a segment or segments with a plurality of functional groups thereon is the PBLCA made in the first three steps of the four step process described in conjunction with the first embodiment. Utilities for the admixture of the third embodiment include drug controlled release functionality including the utilities of the fourth and fifth embodiments.

We turn now to the fourth embodiment of the invention herein, which is directed to a drug release system for biomedical application comprising the copolymer of the first embodiment and/or the admixture of the third embodiment. The drug release system is to release aminoxyl radical or other drug or other biologically active agent incorporated in the polymer or copolymer of the first embodiment or from the admixture of the third embodiment. The drug release system of the fourth embodiment includes the copolymer of the first embodiment or the admixture of the third embodiment, optionally in combination with carrier and/or appropriate other compound or components. The amount of polymeric or copolymeric segment, number of linking molecules (e.g., maleic anhydride), and number of functional groups (e.g., carboxylic acid groups) for the copolymer of the first embodiment, can be tailored with direct cleavable covalent bonding, and conjugation in varying lengths and structures via spacer molecules for attachment of aminoxyl radical as well as other drug or other biologically active agent to obtain controlled release functionality. Moreover, the biocompatible polymer biodegradable polymer or copolymer component of the third embodiment can be tailored by varying the amount of polymeric or copolymeric intermediate capped at one end and having free hydroxyl at the other end, number of linking molecules (e.g., maleic anhydride) and number of functional groups (e.g., carboxylic acid groups) and the ratio of polymer or copolymer to spin label, other drug, or other biologically active agent, to obtain controlled release functionality. The controlled release functionality can be sustained or delayed release functionality. For example, various anti-flammatory drugs (e.g., sirolimus) and anti-proliferative drugs (e.g. paclitaxel), biologics, biologically active agents such as proteins, cytokines, oligonucleotides including antisense oligonucleotides, genes, carbohydrates, hormones, etc., can be applied in conjunction with the polymer materials here, e.g., PBLC-OH PBLC-MA, PBLCA, via direct covalent bonding, e.g. TAM-PBLCA, or ionic bonding by various conjugation techniques using different molecule lengths and structure via spacer molecules to conjugate the drug or other biologically active agent to the polymer backbone; or a polymer drug matrix can be created by admixing spin label or other drug or other biologically active agent with the polymeric component; or strata of drugs and polymeric materials can be structured in layers; or a topcoat can be applied using various hydrogel/drug mixtures to obtain a controlled, sustained drug release local drug delivery system on a stent platform or on microphere (nanoparticle) to provide a microsphere based drug delivery system for systemic application.

We turn now to the fifth embodiment of the invention herein which is a stent associated with, e.g., coated with or made of the drug release or delivery system of the fourth embodiment containing aminoxyl containing radical or toxicity, inflammation or reocclusion ameliorating or preventing other drug or biologically active agent, to provide a drug eluting coating on the stent. Coating on a stent is readily carried out by coating the stent with drug delivery system, in a therapeutically effective amount. The drug delivery systems can be coated onto a stent platform by different coating techniques such as dip coating, spray coating, vacuum coating, spin coating, etc., to an appropriate thickness to permit delivery of a drug or other biologically active agent in a pharmacologically suitable and therapeutically effective amount over a sustained period. Coating with TAM-PBLCA can be carried out, for example, by melt coating under inert gas, e.g., nitrogen, without degradation causing external stress (e.g., without high humidity), or solution coating from an aprotic or other solvent, e.g., dioxane, tetrahydrofuran, dimethyl sulfoxide or chloroform. The drug delivery system herein can also be formed in a mesh or tubular configuration which can be placed over a stent and which expands with the stent to provide a wider range of coverage of an artery wall. The drug delivery system can also be configured in the form of a stent which would be expanded via a balloon and cross linked into a rigid form by use of UV light.

For attachment of other drug molecule residue or other biologically active agent residue, drugs or other biologically active agents with functional groups reactive with functional groups of the biodegradable polymer are reacted in place of spin labels.

The weight average molecular weights set forth herein are determined by gel permeation chromatography versus monodispersed polystyrene standards.

In the expression "some or each" used herein, "some" means more than one and less than all, and the word "each" connotes all.

The invention herein is illustrated in the following working examples.

EXAMPLE I

Lactide (7.5 moles), ε-caprolactone (3 moles), benzyl alcohol (1 mole) and stannous octoate (0.5% by weight) were added into a Pyrex polymerization tube. This was followed by argon-filling of head space of the polymerization tube and application of vacuum to said head space for several times whereupon the polymerization tube was vacuum sealed. The sealed tube was placed in an oil bath at 130° C. for 48 hours to obtain melt ring opening polymerization of lactide and ε-caprolactone and provide poly(lactide-co-ε-caprolactone) which is capped with benzyl alcohol at one end and has free hydroxyl at the other end, i.e., PBLC-OH. The sealed tube was removed from the oil bath and cooled to room temperature, whereupon the resulting product was removed from the polymerization tube by dissolving in chloroform. The resulting solution was poured into excess petroleum ether to precipitate the polymer. The precipitate was washed four times with distilled water and dried over $P_2O_5$ under vacuum at room temperature until constant weight was obtained.

Another run was carried out as above except that the reactants were present in amounts as follows: Lactide (17.5 moles), ε-caprolactone (7 moles), benzyl alcohol (1 mole). Stannous octoate was present in amount of 0.5% by weight.

The results for the two runs are set forth in Table 1 below where $M_n$ is number average molecular weight, $M_w$ is weight average molecular weight, and $M_p$ is peak molecular weight (i.e., the PBLC-OH weight average molecular weight at the peak of the GPC curves for the PBLC-OH samples of Table 1).

TABLE 1

| | Feed Molar Ratio | | Molecular Weight of PBLC-OH | | | |
|---|---|---|---|---|---|---|
| Run | Benzyl Alcohol | ε-caproyl (C unit) | α-oxy-propionyl (L unit) | $M_n$ (×10³) | $M_w$ (×10³) | $M_p$ (×10³) | Polydispersity ($M_w/M_n$) |
| 1 | 1 | 3 | 15 | 1.76 | 3.05 | 2.85 | 1.73 |
| 2 | 1 | 7 | 35 | 3.28 | 4.73 | 4.80 | 1.44 |

The molar ratio of —$CH_2OH$ end group to —$CH(CH_3)$—OH end group in PBLC-OH obtained in Run 2 was 1/19.62. The compositional ratio of ε-oxycaproyl unit (C unit) to α-oxyprionyl unit (L unit) obtained in Run 2 was 1/4.53 whereas the feed molar ratio was 1/5 demonstrating that the rate of polymerization of the ε-caprolactone monomer was higher than the rate of polymerization of the lactide monomer. In the product obtained in Run 2, 95% of the PBLC-OH copolymer had α-oxypropionyl end group. The 95% α-oxyproprionyl end group amount was obtained due both to the feed molar ratio for Run 2 in Table 1 and because the polymerization rate of ε-caprolactone was higher than the polymerization rate for lactite monomer for the polymerization conditions used. If the feed molar ratio were instead 35 moles C unit and 7 moles L unit, the percentage of PBLC-OH molecules with lactide end groups will increase but the level of increase will be limited because of the aforedescribed relative polymerization rates.

PBLC-OH (0.01 moles) from Run 2 and maleic anhydride (0.05 moles), 1:5 molar ratio, were placed in a three-neck flask under $N_2$ atmosphere at 130° C. for 24 hours. Then, excess maleic anhydride was distilled off at 130° C. under vacuum, and the reaction mixture was then dissolved in chloroform The chloroform solution was extracted with water three times to remove residual maleic anhydride and dried with anhydrous $MgSO_4$ overnight. Purified PBLC-Ma was obtained by precipitating the water-extracted chloroform solution in excess petroleum ether and drying in vacuum at room temperature. Fifty-four percent of the hydroxyl end groups in PBLC-OH copolymer were reacted with maleic anhydride and converted to double bond functionality (87% maleic monoester acid and 13% fumaric monoester acid due to a rearrangement reaction).

PBLC-Ma (1.98 g), acrylic acid (3.0 g) and AIBN (0.0335 g) (1.1% by weight of acrylic acid) were dissolved in 20 ml of dioxane at room temperature in a three-neck flask under $N_2$. The resulting solution was heated to 60° C. for 5 hours. After removal of most of the solvent by distillation at 120° C., the reaction mixture was precipitated in cold water to obtain separation from acrylic acid homopolymer by-product. The precipitate, PBLCA, was filtered, washed with cold water three times and dried over $P_2O_5$ under vacuum at room temperature.

PBLCA (1.1392 g) was dissolved in 20 ml dioxane at 50° C. and 0.2851 g of N,N'-carbonyl diimidazole was then added. After 15 minutes, 0.3140 g of 4-amino-2,2,6,6-tetramethylpiperidine 1-oxy (TEMPAMINE) dissolved in 5 ml dioxane was added slowly to the reaction mixture at 50° C. The reaction mixture was vigorously stirred for several hours at 50° C. The resulting solution was added dropwise into petroleum ether to precipitate TAM-PBLCA. The resulting precipitate was stirred in 100 ml of water for 3 hours at room temperature to remove excess TEMPAMINE, N,N'-carbonyl diimidazole and imidazole (produced during reaction), filtered, washed four times with water and then dried over $P_2O_5$ in vacuum at room temperature. The TEMPAMINE content in the TAM-PBLCA was 8.32% by weight.

The molecular weight results obtained in each stage, PBLC-OH from Run 2, PBLC-Ma, PBLCA and TAM-PBLCA, are set forth in Table 2 below:

TABLE 2

| Polymers | $M_n$(×10³) | $M_w$(×10³) | $M_p$(×10³) | Polydispersity ($M_w/M_n$) |
|---|---|---|---|---|
| PBLC-OH | 3.28 | 4.73 | 4.80 | 1.44 |
| PBLC-Ma | 2.93 | 7.05 | 6.53 | 2.41 |
| PBLCA | 4.61 | 7.17 | 9.21 | 1.56 |
| TAM-PBLCA | 1.61 | 4.55 | 4.05 | 2.83 |

The TAM-PBLCA has the utilities of the components with moieties containing animoxyl-containing radical, described in U.S. Pat. No. 5,516,881.

EXAMPLE II

A drug release system is prepared by admixing PBLCA with TEMPAMINE (10 parts PBLCA to 1 part TEMPAMINE) or by admixing PBLCA with paclitaxel (50 parts PBLCA to 1 part paclitaxel). The former has utilities described in U.S. Pat. No. 5,516,881 for components with moieties containing aminoxyl-containing radicals described in U.S. Pat. No. 5,516,881. The latter has anti-tumor utility.

EXAMPLE III

A stent is dip coated with TAM-PBLCA by dipping it in a solution of TAM-PBLCA in dioxane (1 g TAM-PBLCA in 20 ml dioxane) or other suitable solvent and evaporating the solvent. The TAM-PBLCA coated stent deployed after angioplasty is associated with reduced inflammation compared to a conventional stent.

Variations

Many variations of the above will be obvious to those skilled in the art. Therefore, the invention is defined in the claims.

What is claimed is:

1. Biocompatible biodegradable copolymer comprising a polymeric or copolymeric segment which is capped at one end to prevent reaction at that end with unsaturated functional group containing compound and linked at the other end to a polymeric or copolymeric segment having a plurality of functional groups pendant thereto, some or each of the functional groups having been reacted thereby attaching a moiety containing an aminoxyl-containing radical or thereby attaching a moiety comprising other drug molecule residue or a moiety comprising other biologically active agent residue.

2. The biocompatible biodegradable copolymer of claim 1 where the plurality of functional groups are a plurality of carboxyl groups with some or each of the carboxyl groups having been reacted thereby attaching via an amide, ester, or oxycarbonyl linkage a moiety containing an aminoxyl-containing radical, a moiety comprising other drug molecule residue or a moiety comprising other biologically active agent residue.

3. The biocompatible biodegradable copolymer of claim 2 where provision of said linkage at the other end comprises incorporating an unsaturated group to provide a double bond functionalized polymer or copolymer and where provision of said linkage is by polymerizing unsaturated group containing monomer in the presence of the double bond functionalized polymer or copolymer.

4. The biocompatible biodegradable polymer of claim 2 which is formed from a starting material polymer or copolymer which contains a hydrolyzable ester or nitrogen-phosphorus linkage and which is capped at one end to prevent reacting at that end with unsaturated functional group containing compound and has a free hydroxyl at the other end and by converting the hydrogen of the free hydroxyl to carbonyl linked to terminal moiety containing unsaturated group and reacting unsaturated group of the terminal moiety with unsaturated carboxyl group containing compound or polymer thereof to provide an end segment with a plurality of carboxyl groups thereon and modifying some or each of the carboxyl groups to provide moiety containing an aminoxyl-containing radical or a moiety comprising other drug molecule residue or a moiety comprising other biologically active agent residue in place of the hydroxyl moiety of carboxyl group.

5. The biocompatible biodegradable polymer of claim 4 where some or each of the carboxyl groups have been reacted thereby attaching via an amide, ester, or oxycarbonyl linkage the moiety containing an aminoxyl-containing radical or the moiety comprising other drug molecule residue or the moiety comprising the other biologically active agent.

6. The biocompatible biodegradable polymer of claim 5 constituting a biocompatible biodegradable polymer incorporating drug controlled release functionality.

7. The biocompatible biodegradable copolymer of claim 2 where said polymeric or copolymeric segment is selected from the group consisting of polylactide, polycaprolactone, polyglycolide, poly(3-hydroxybutyrate) and their copolymers and the polymeric or copolymeric segment is capped at one end to prevent reaction at that end with unsaturated functional group containing compound and is linked at the other end to a segment comprising polyacrylic acid with some or each of the carboxyl groups thereon modified to provide a moiety containing an aminoxyl-containing radical or a moiety comprising other drug molecule residue or a moiety comprising other biologically active agent in place of hydroxyl moiety of the carboxyl group.

8. The biocompatible biodegradable copolymer of claim 7 where the linkage is provided by reacting linking agent selected from the group consisting of maleic anhydride, acryloyl chloride, methacryloyl chloride and allyl isocyanate with hydroxyl of poly(lactide-co-$\epsilon$-caprolactone) which is capped at one end to prevent reaction at that end with said linking agent and is hydroxyl terminated at the other end to provide a double bond functionalized poly(lactide-co-$\epsilon$-caprolactone) and free radical polymerizing acrylic acid in the presence of the double bond functionalized poly(lactide-co-$\epsilon$-caprolactone).

9. The biocompatible biodegradable polymer of claim 1 constituting a biocompatible biodegradable polymer incorporating drug controlled release functionality.

10. A drug release system for biomedical application comprising the copolymer of claim 1.

11. A stent associated with or formed of the drug release system of claim 10 to provide a stent with a drug eluting system.

12. The biocompatible biodegradable compound of claim 1 where the capping is by providing an ester group at the capped end.

13. The biocompatible biodegradable compound of claim 12 where the ester group is a benzyl ester group.

14. Poly(lactide-co-$\epsilon$-caprolactone) which is capped at one end to prevent reaction at that end with unsaturated functional group containing compound and is linked at the other end to a segment comprising polyacrylic acid and/or other polyacid which has carboxyl functional groups which can be reacted to attach moiety containing an aminoxyl-containing radical or moiety comprising other drug molecule residue or moiety comprising other biologically active agent residue in place of hydroxyl group of carboxyl functional group.

15. The poly(lactide-co-$\epsilon$-caprolactone) of claim 14 when the capping is by providing an ester group at the capped end.

16. The poly(lactide-co-$\epsilon$-caprolactone) of claim 15 where the ester group is a benzyl ester group.

17. Biocompatible biodegradable polymer or copolymer which is capped by reaction during polymerization with a capping agent at one end to prevent reaction at that end and has a free hydroxyl at the other end.

18. The biocompatible biodegradable polymer or copolymer of claim 17 where the capping is by providing an ester group at the capped end.

19. The biocompatible biodegradable polymer or copolymer of claim 18 where the ester group is a benzyl ester group.

20. An admixture of a biocompatible biodegradable polymer or copolymer which is capped at one end to prevent reaction at that end with unsaturated functional group containing compound and contains at other end a segment or segments with a plurality of functional groups thereon and a spin label and/or other drug molecule and/or other biologically active agent, in a weight ratio of polymer or copolymer to spin label and other drug molecule and other biologically active agent ranging from 1:99 to 99:1, to permit a polymer spin label/other drug/other biologically active agent matrix for delivery of the spin label, other drug and/or other biologically active agent.

21. A drug release system for biomedical application comprising the admixture of claim 20.

22. The admixture of claim 20 where the capping is by providing an ester group at the capped end.

23. The admixture of claim 22 where the ester group is a benzyl ester group.

* * * * *